United States Patent
Lin et al.

(10) Patent No.: US 7,094,282 B2
(45) Date of Patent: Aug. 22, 2006

(54) CALCIUM PHOSPHATE CEMENT, USE AND PREPARATION THEREOF

(75) Inventors: Jiin-Huey Chern Lin, Winnetka, IL (US); Chien-Ping Ju, Carbondale, IL (US); Wen-Cheng Chen, Tainan Hsien (TW)

(73) Assignee: Calcitec, Inc., Austin, TX (US)

( * ) Notice: Subject to any disclaimer, the term of this patent is extended or adjusted under 35 U.S.C. 154(b) by 154 days.

(21) Appl. No.: 10/414,582

(22) Filed: Apr. 16, 2003

(65) Prior Publication Data

US 2004/0031420 A1 Feb. 19, 2004

Related U.S. Application Data

(63) Continuation-in-part of application No. 09/615,384, filed on Jul. 13, 2000, now abandoned.

(51) Int. Cl.
*A61K 33/42* (2006.01)

(52) U.S. Cl. ............. 106/35; 106/690; 623/23.62; 428/403; 428/404

(58) Field of Classification Search .......... 106/35, 106/690; 623/23.62; 428/403, 404
See application file for complete search history.

(56) References Cited

U.S. PATENT DOCUMENTS

| 3,679,360 | A | 7/1972 | Rubin et al. |
| 4,371,484 | A | 2/1983 | Inukai et al. |
| 4,612,053 | A | 10/1986 | Brown et al. |
| RE33,161 | E | 2/1990 | Brown et al. |
| 5,017,518 | A | 5/1991 | Hirayama et al. |
| 5,149,368 | A | 9/1992 | Liu et al. |
| 5,164,187 | A | 11/1992 | Constantz et al. |
| 5,180,426 | A | 1/1993 | Sumita |

(Continued)

FOREIGN PATENT DOCUMENTS

| JP | 06-228011 | 8/1994 |
| WO | WO 03/055418 | 7/2003 |

OTHER PUBLICATIONS

Sugawara et al., "Calcium Phosphate Cement: An In Vitro study of Dentin Hypersensitivity", The Journal of the Japanese Society for Dental Materials and Devices, 1989, vol. 8, pp. 282–294.

Pickel et al., "The Effect of a Chewing Gum Containing Dicalcium Phosphate on Salivary Calcium and Phosphate", Ala. J. Med. Sci. 1965, vol. 2, pp. 286–287.

(Continued)

*Primary Examiner*—C. Melissa Koslow
(74) *Attorney, Agent, or Firm*—Meyertons, Hood, Kivlin, Kowert & Goetzel, P.C.; Eric B. Meyertons

(57) ABSTRACT

A calcium phosphate cement suitable for use in dental and bone prosthesis is disclosed, which include calcium phosphate particles having a diameter of 0.05 to 100 microns, wherein said calcium phosphate particles on their surfaces have whiskers or fine crystals having a width ranging from 1 to 100 nm and a length ranging from 1 to 1000 nm.

34 Claims, 11 Drawing Sheets

U.S. PATENT DOCUMENTS

| | | |
|---|---|---|
| 4,959,104 A | 8/1994 | Iino et al. |
| 5,342,441 A | 8/1994 | Mandai et al. |
| 5,476,647 A | 12/1995 | Chow et al. |
| 5,496,399 A * | 3/1996 | Ison et al. .................... 106/35 |
| 5,503,164 A | 4/1996 | Friedman |
| 5,522,893 A | 6/1996 | Chow et al. |
| 5,525,148 A | 7/1996 | Chow et al. |
| 5,536,575 A | 7/1996 | Imura et al. |
| 5,542,973 A | 8/1996 | Chow et al. |
| 5,545,254 A | 8/1996 | Chow et al. |
| 5,550,172 A | 8/1996 | Regula et al. |
| 5,569,490 A | 10/1996 | Imura et al. |
| 5,652,016 A | 7/1997 | Imura et al. |
| 5,683,496 A | 11/1997 | Ison et al. |
| 5,695,729 A | 12/1997 | Chow et al. |
| 5,697,981 A | 12/1997 | Ison et al. |
| 5,766,669 A | 6/1998 | Pugh et al. |
| 5,814,681 A | 9/1998 | Hino et al. |
| 5,820,632 A | 10/1998 | Constantz et al. |
| 5,846,312 A | 12/1998 | Ison et al. |
| 5,891,448 A | 4/1999 | Chow et al. |
| 5,899,939 A | 5/1999 | Boyce et al. |
| 5,954,867 A | 9/1999 | Chow et al. |
| 5,964,932 A | 10/1999 | Ison et al. |
| 5,976,234 A | 11/1999 | Chow et al. |
| 5,993,535 A | 11/1999 | Sawamura et al. |
| 5,997,624 A | 12/1999 | Chow et al. |
| 6,013,591 A | 1/2000 | Ying et al. |
| 6,117,456 A | 9/2000 | Lee et al. |
| 6,123,731 A | 9/2000 | Boyce et al. |
| 6,162,258 A | 12/2000 | Scarborough et al. |
| 6,325,987 B1 | 4/2001 | Sapieszko et al. |
| 6,277,149 B1 | 8/2001 | Boyle et al. |
| 6,294,041 B1 | 9/2001 | Boyce et al. |
| 6,294,187 B1 | 9/2001 | Boyce et al. |
| 6,325,992 B1 | 12/2001 | Chow et al. |
| 6,332,779 B1 | 12/2001 | Boyce et al. |
| 6,340,648 B1 | 1/2002 | Imura et al. |
| 6,379,453 B1 | 4/2002 | Lin et al. |
| 6,440,444 B1 | 8/2002 | Boyce et al. |
| 6,478,825 B1 | 11/2002 | Winterbotton et al. |
| 6,530,955 B1 | 3/2003 | Boyle et al. |
| 6,547,866 B1 | 4/2003 | Edwards et al. |
| 6,616,742 B1 | 10/2003 | Lin et al. |
| 6,648,960 B1 | 11/2003 | Lin et al. |
| 6,840,995 B1 | 1/2005 | Lin et al. |
| 2002/0019635 A1 | 2/2002 | Wenstom, Jr. et al. |
| 2002/0073894 A1 | 6/2002 | Genge et al. |
| 2002/0137812 A1 | 9/2002 | Chow et al. |
| 2003/0019396 A1 | 1/2003 | Edwards et al. |
| 2003/0031698 A1 | 2/2003 | Roeder et al. |
| 2003/0078317 A1 | 4/2003 | Lin et al. |
| 2003/0121450 A1 | 7/2003 | Lin et al. |
| 2004/0003757 A1 | 1/2004 | Lin et al. |
| 2004/0031420 A1 | 2/2004 | Lin et al. |
| 2004/0175320 A1 | 9/2004 | Lin et al. |
| 2004/0180091 A1 | 9/2004 | Lin |
| 2004/0186481 A1 | 9/2004 | Lin et al. |

OTHER PUBLICATIONS

Matsuya et al., "Effects of pH on the Reactions of Tetracalcium Phosphate and Dicalcium Phosphate", IADR Abstact 1991.

Sugawara et al., "Formation of Hydroxyapatite in Hydrogels from Tetracalcium Phosphate/Dicalcium Phosphate Mixtures,"J. Nihon. Univ. Sch. Dent., vol. 31, pp. 372–381.

Hong et al., The Periapical Tissue Reactions to a Calcium Phosphate Cement in the Teeth of Monkeys, J. Biomed Mater Res. Apr. 1991, vol. 25(4), pp. 485–498.

DeRijk, et al., "Clinical Evaluation of a Hydroapatite Precipitate for the Treatment of Dentinal Hypersensitivity, Biomedical Engineering v. Recent Developments," Proc of 5th Southern Biomedical Engineering Conference, 1986, pp. 336–339. (Pergamon Press, New York).

Groninger et al., "Evaluation of the Biocompatibility of a New Calcium Phosphate Setting Cement," J. Dent. Res. 1984, 63 Abst. No. 270(4 pages).

Constantino et al., Evaluation of a New Hydroxyapatite Cement: Part III, Cranioplasty ina Cat Model, The Fifth Intl. Symposium on Facial Plastic Reconstructive Surgery of the Head and Neck, Toronto, Canada 1989. (18 pages).

Shindo, et al., "Facial Skeletal Augmentation Using Hydroxyapatite Cement," Arch.Otolaryngol. Head Neck Srug. 1993, vol. 119, pp. 185–190.

Briner et al., "Significance of Enamel Remineralization", J. Dent. Res. 1974, vol. 53, pp. 239–243.

Silverstone, "Remineralizatioin Phenomena", Caries Res. 1977, vol. 11 (Suppl. 1), pp. 59–84.

Constantino et al., "Hydroxyapatite Cement—Basic Chemistry and Histologic Properties," Arch. of Otolaryngology-–Head & Neck Surgery, 1991, vol. 117, pp. 379–394.

Friedman et al., "Hydroxyapatite Cement II. Obliteration and Reconstruction of the Cat Frontal Sinus," Arch. of Otolaryngology—Heady & Neck Surgery, 1991, vol. 117, pp. 385–389.

Constantino et al., "Experimental Hydroxyapatite Cement Cranioplasty," Plastic and Reconstructive Surgery, 1992, vol. 90, No. 2, pp. 174–185.

Miyazaki et al., "An Infrared Spectroscopic Study of Cement Formation of Polymeric Calcium Phosphate Cement," Jour of the Jap. Scoety for Dent Mats & Devices, 1992, vol. II, No. 2, (8 pages).

Driskell et al., "Development of Ceramic and Ceramic Composite Devices for Maxillofacial Applications", J. Biomed. Mat. Res. 1972, vol. 6, pp. 345–361.

Hiatt et al., "Root Preparation I. Obduration of Dentinal Tubules in Treatment of Root Hypersensitivity", J. Periodontal, 1972, vol. 43, pp. 373–380.

Patel et al., "Solubility of $CaHPO_4 2H_2O$ in the Quaternary System $Ca(OH)_2$—$H_3PO_4$—NaCl—$H_2O$ at 25° C., " J. Res. Nat. Bur. Stands. 1974, vol. 78A, pp. 678–681.

Salyer et al., "Porous Hydroxyapatite as an Onlay Bone–Graft Substitute for Maxillofacial Surgery,"Presented at the 54th Annual Scientific Meeting of the American Society of Plastic and Reconstructive Surgeons, Kansas City, Missouri, 1985, pp. 236–244.

Kenney et al., "The Use of Porous Hydroxyapatite Implant in Periodontal Defects," J. Periodontal, 1988, pp. 67–72.

Zide et al., "Hydroxyapatite Cranioplasty Directly Over Dura," J. Oral Maxillofac Surg. 1987, vol. 45, pp. 481–486.

Waite, et al., "Zygomatic Augmentation with Hydroxyapatite," J. Oral Maxillofac Surg 1986, pp. 349–352.

Verwoerd, et al., "Porous Hydroxyapatite–perichondrium Graft in Cricoid Reconstruction, Acta Otolaryngol" 1987, vol. 103, pp. 496–502.

Grote, "Tympanoplasty With Calcium Phosphate," Arch Otolaryngology, 1984, vol. 110, pp. 197–199.

Kent et al., "Alveolar Ridge Augmentation Using Nonresorbable Hydroxyapatite with or without Autogenous Cancellous Bone," J. Oral Maxillofac Surg 1983, vol. 41, pp. 629–642.

Piecuch, "Augmentation of the Atrophic Endentulous Ridge with Porus Replamineform Hydroxyapatite (Interpore–200)", Dental Clinics of North America 1985, vol. 30(2), pp. 291–305.

Misch, "Maxillary Sinus Augmentation for Endosteal Implants: Organized Alternative Treatment Plants,"Int J. Oral Implant 1987, vol 4(2), pp. 49–58.

Chohayeb, A. A. et al., "Evaluatiion of Calcium Phosphate as a Root Canal Sealer–Filler Material," J. Endod. 1987, vol. 13, pp. 384–386.

Brown et al., "Crystallography of Tetracalcium Phosphate, "Journal of Research of the National Bureau of Standards. A. Physics and Chemistry. 1965, vol. 69A, pp. 547–551.

Sanin et al. "Particle Size Effects on pH and Strength of Calcium Phosphate Cement,"IADR Abstract 1991.

Chow et al., "X–ray Diffraction and Electron Microscopic Characterization of Calcium Phosphate Cement Setting Reactions,"IADR Abstract, 1987. (1 page).

Block et al "Correction of Vertical Orbital Dystopia with a Hydroxyapatite Orbital Floor Graft,"J. Oral Maxillofac Surg 1988, vol. 46, pp. 420–425.

Brown, "Solubilites of Phosphates and Other Sparingly Soluble Compounds", Environmental Phosphorous Handbook 1973, pp. 203–239. (John Wiley & Sons, New York).

Matsuya et al., "Effects of pH on the Reactions of Tetracalcium Phosphate and Dicalcium Phosphate", IADR Abstract 1991. (1 page).

Briner et al., "Significance of Enamel Remineralization", J. Dent. Res. 1974, vol. 53, pp. 239–243.

Chow, "Development of Self–Setting Calcium Phosphate Cements", Journal of The Ceramic Society of Japan, 1991, vol. 99(10), pp. 954–964.

Brown et al., A New Calcium Phosphate, Water Setting Cement, Cements Research Progress 1986, P. W. Brown, Ed., Westerville, Ohio: American Ceramic Society, 1988, pp. 352–379.

Sugawara et al., "Evaluation of Calcium Phosphate as a Root Canal Sealer–Filler Material"IADR/AADR Abstract, 1987, (3 pages).

Sugawara et al., "In Vitro Evaluation of the Sealing Ability of a Calcium Phosphate Cement When Used as a Root Canal Sealer Filler,"J. Edondontics, vol. 16, pp. 162–165.

Chow, "Calcum Phosphate Materials: Reactor Response"Adv Dent Res 1988, vol 2(1), pp. 181–184.

Fukase et al., "Setting Reactions and Compressive Strengths of Calcium Phosphate Cements", J. Dent Res 1990, vol. 69(12), pp. 1852–1856.

Miyazaki et al., "Chemical Change of Hardened PCA/CPC Cements in Various Storing Solutions", The Journal of the Japanese Soc. for Dental Materials and Devices, 1992, vol. 11, No. 2, pp. 48–64.

* cited by examiner

CALCIUM PHOSPHATE CEMENT, USE AND PREPARATION THEREOF

RELATED APPLICATION

This application is a continuation-in-part and claims the benefit of priority under 35 U.S.C. § 120 of U.S. application Ser. No. 09/615,384, filed Jul. 13, 2000, now abandoned. The disclosure of the prior application is considered part of and is incorporated by reference in the disclosure of this application.

FIELD OF THE INVENTION

The present invention is related to a calcium phosphate cement, and in particular a fast-setting calcium phosphate cement, for use in dental and bone prosthesis.

BACKGROUND OF THE INVENTION

A calcium phosphate cement (abbreviated as CPC) has been widely used as an implant or filling material in dental and bone prosthesis, and its technical details can be found in many patents, for examples U.S. Pat. Nos. 4,959,104; 5,092,888; 5,180,426; 5,262,166; 5,336,264; 5,525,148; 5,053,212; 5,149,368; 5,342,441; 5,503,164; 5,542,973; 5,545,254; 5,695,729 and 5,814,681. In general, the prior art calcium phosphate cements suffer one or more drawbacks as follows: 1) additives having a relatively poor bioactivity being required; 2) a complicated preparation process; 3) an undesired setting time or working time of CPC, which are difficult to be adjusted; 4) not capable of being set to a desired shape in water, blood or body fluid; and 5) poor initial strength after setting of the CPC.

SUMMARY OF THE INVENTION

An object of the present invention is to provide a calcium phosphate cement.

Another object of the present invention is to provide a calcium phosphate cement comprising particles having whiskers or fine crystals on surfaces of the particles.

Still another object of the present invention is to provide a process for preparing a calcium phosphate cement.

A further object of the present invention is to provide a method of treating a bone or a tooth having a defect in a patient by using a calcium phosphate cement.

In order to accomplish the above objects of the present invention a calcium phosphate cement prepared in accordance with the present invention comprises calcium phosphate particles having a diameter of 0.05 to 100 microns, wherein said calcium phosphate particles on their surfaces have whiskers or fine crystals having a width ranging from 1 to 100 nm and a length ranging from 1 to 1000 nm. By adjusting the diameter of the calcium phosphate particles, the width and/or the length of the whiskers or fine crystals, the inventors of the present invention are able to adjust the working time and/or the setting time of the calcium phosphate cement of the present invention to conform to requirements for various purposes. Moreover, the calcium phosphate cement of the present invention is fast-setting, and is non-dispersive in water or an aqueous solution.

DETAILED DESCRIPTION OF THE INVENTION

Figure 1:
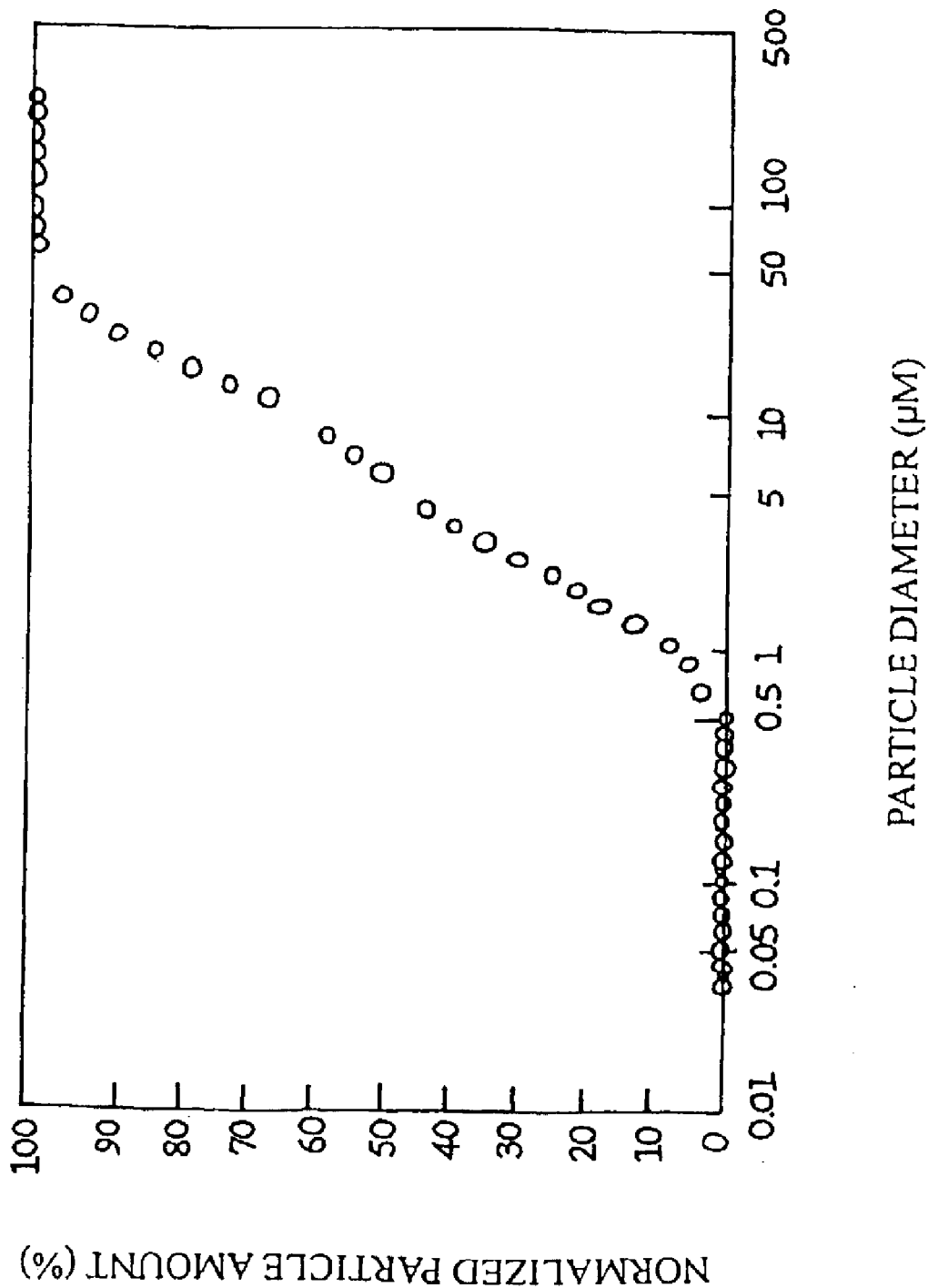
FIG. 1 is a normalized particle amount (%) versus particle diameter (μm) plot showing a particle diameter distribution of a calcium phosphate cement (CPC) prepared in accordance with the following Example 6 of the present invention.

A suitable process for preparing the calcium phosphate cement of the present invention comprises mixing a calcium phosphate powder or small pieces of calcium phosphate with a wetting agent, and controlling growth of whiskers or fine crystals on surfaces of said calcium phosphate powder or small pieces of calcium phosphate by an controlling treatment.

Suitable calcium phosphates for use as the calcium phosphate powder or small pieces of calcium phosphate in the present invention can be any known calcium phosphates such as calcium dihydrogen phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium polyphosphate, calcium metaphosphate, anhydrous tricalcium phosphate, tricalcium phosphate hydrate, apatite, hydroxyapatite, a mixture thereof and an adduct thereof. Moreover, the shape of the calcium phosphate powder and the shape of the small pieces of calcium phosphate are not limited, which can be spherical or irregular; and the crystal structure thereof can be single crystal, polycrystal, mixed crystals, semi-crystal, or amorphous.

The process for preparing the calcium phosphate cement preferably further comprises grinding the resulting product from the controlling treatment to form calcium phosphate particles having a diameter of 0.05 to 100 microns, wherein said whiskers or fine crystals have a width ranging from 1 to 100 nm and a length ranging from 1 to 1000 nm.

Said controlling treatment is a vacuuming treatment, an organic solvent treatment, a microwave treatment, a heating treatment, or any other treatments which can controll growth of whiskers or fine crystals on surfaces of said calcium phosphate powder or small pieces of calcium phosphate.

Said wetting agent is used to wet the calcium phosphate powder or small pieces of calcium phosphate, and preferably is a diluted aqueous solution containing phosphoric acid or phosphate. The amount of said wetting agent mixed with the calcium phosphate powder or small pieces of calcium phosphate, in general, should be enough to wet substantially all the calcium phosphate powder or small pieces of calcium phosphate. However, it is not necessarily the case when said controlling treatment is the organic solvent treatment, where a water miscible organic solvent is added to the mixture of said wetting agent and said calcium phosphate powder or small pieces of calcium phosphate to form a paste for a subsequent processing step.

Preferably, said wetting agent is a diluted aqueous solution containing more than 20 ppm of phosphoric acid or phosphate, more preferably more than 50 ppm, and most preferably more than 100 ppm of phosphoric acid or phosphate.

Preferably, the process for preparing the calcium phosphate cement of the present invention comprises soaking said calcium phosphate powder or said small pieces of calcium phosphate with said diluted aqueous solution containing more than 100 ppm of phosphoric acid or phosphate, and carrying out (a) said heating treatment comprising drying the resulting soaked calcium phosphate powder or soaked small pieces of calcium phosphate at a temperature higher than 45° C.; (b) said vacuuming treatment comprising drying the resulting soaked calcium phosphate powder or soaked small pieces of calcium phosphate under vacuum; or (c) said microwave treatment comprising drying the resulting soaked calcium phosphate powder or soaked small pieces of calcium phosphate by microwave heating. More preferably, the resulting soaked calcium phosphate powder or soaked small pieces of calcium phosphate is well mixed to form a uniform mixture prior to being subjected to treatment (a), (b) or (c).

Alternatively, the process for preparing the calcium phosphate cement of the present invention comprises mixing said calcium phosphate powder or said small pieces of calcium phosphate with said diluted aqueous solution containing more than 100 ppm of phosphoric acid or phosphate, and carrying out said organic solvent treatment comprising mixing the mixture of said wetting agent and said calcium phosphate powder or small pieces of calcium phosphate with a water miscible organic solvent, and drying the resulting mixture under vacuum. Preferably, said organic solvent treatment is carried out while stirring, and more preferably, the mixture of said diluted aqueous solution containing more than 100 ppm of phosphoric acid or phosphate and said calcium phosphate powder or small pieces of calcium phosphate is well mixed prior to being subjected to said organic solvent treatment.

Preferably, said calcium phosphate particles of the calcium phosphate cement of the present invention have a diameter of 0.2 to 80 microns, and more preferably 0.5 to 50 microns.

The width of a whisker means an average value of lateral cross-sectional diameters of the whisker, and the width of a fine crystal means an average value of the first 30% of the diameters of the fine crystal, which are shorter than the other 70% thereof. The length of a fine crystal means an average value of the last 30% of the diameters of the fine crystal, which are longer than the other 70% thereof.

Preferably, said whiskers or fine crystals have a width ranging from 2 to 70 nm and a length ranging from 5 to 800 nm, and more preferably a length ranging from 10 to 700 nm.

Preferably, said calcium phosphate particles have a molar ratio of calcium to phosphate ranging from 0.5 to 2.5, more preferably 0.8 to 2.3, and most preferably 1.0 to 2.2.

The calcium phosphate cement of the present invention is biocompatible and a paste made therefrom is non-dispersive in water, which has a working time from several minutes to hours and a setting time from a few minutes to hours. Consequently, the calcium phosphate cement of the present invention is extremely suitable for use as an implant or filling material in dental or bone prosthesis, where the paste must contact water, blood or body fluid. Particularly, the paste made from the calcium phosphate cement of the present invention is able to be directly injected into a bone defect or cavity as an implant or filling material.

The present invention also discloses a method of treating a bone or a tooth having a defect in a patient, comprising mixing the calcium phosphate cement of the present invention and a hardening-promoter-containing aqueous solution to form a paste, and a) injecting said paste into a bone defect or cavity of said patient or b) shaping said paste and implanting the resulting shaped paste into a bone defect or cavity of said patient.

In the method of the present invention, said calcium phosphate cement may further comprise a growth factor, a bone morphology protein or a pharmaceutical carrier, or said hardening-promoter-containing aqueous solution further comprises a growth factor, a bone morphology protein or a pharmaceutical carrier.

Said hardening-promoter-containing aqueous solution can be an aqueous solution comprising any known compounds or compositions which enable the solidification of calcium phosphate, for examples phosphates, calcium salts, and fluorides. That is said hardening-promoter-containing aqueous solution may be an aqueous solution comprising phosphate ions, calcium ions, fluorine ions, or phosphate ions together with fluorine ions as a hardening promoter.

The content of said hardening promoter in said hardening-promoter-containing aqueous solution has no special limitation, but preferably ranges from 1 mM to 3 M, and more preferably from 10 mM to 1 M.

The mixing ratio of the calcium phosphate cement of the present invention and said hardening-promoter-containing aqueous solution is not restricted to any particular ranges; however, the amount of said hardening-promoter-containing aqueous solution mixed should be sufficient to provide substantial wetting of the calcium phosphate cement of the present invention. It should be noted that more water can be supplied in-situ from saliva or body fluid, when the paste is injected or implanted into the bone defect or cavity. Further, the content of said hardening promoter in said hardening-promoter-containing aqueous solution should be adjusted to a higher level corresponding to a less amount of said hardening-promoter-containing aqueous solution being mixed.

EXAMPLE 1

Heating Treatment 5 g of $Ca(H_2PO_4)_2.H_2O$ powder and 1.6 ml of 25 mM phosphoric acid aqueous solution were mixed, and stirred for one minute. The resulting mixture was placed into an oven at 50° C. for 15 minutes, and the resulting dried mixture was mechanically ground for 20 minutes to fine particles after being removed from the oven. 1 g of the fine particles and 0.4 ml of phosphate aqueous solution (1.0 M, pH=6.0) were mixed to form a paste, which was tested every 30 seconds to determine the working time and the setting time. The setting time is the time required when a 1 mm diameter pin with a load of ¼ pounds can be inserted only 1 mm deep into the surface of the paste. The working time is the time after which the paste is too viscous to be stirred. The working time of the paste of this example is 30 minutes and the setting time thereof is one hour.

The paste was placed in a relatively large amount of deionized water immediately following the formation thereof, and it was observed that the paste was non-dispersive in deionized water.

EXAMPLE 2

Vacuuming Treatment 5 g of $CaHPO_4$ (DCPA) powder and 1.2 ml of 25 mM phosphoric acid aqueous solution were mixed, and stirred for one minute. The resulting mixture was placed in a vacuum environment of −100 Pa for 30 minutes, and the resulting dried mixture was mechanically ground for 20 minutes to fine particles. 1 g of the fine particles and 0.4 ml of phosphate aqueous solution (1.0 M, pH=6.0) were mixed to form a paste, which was tested every 30 seconds to determine the working time and the setting time. The working time of the paste of this example is 20.5 minutes and the setting time thereof is 24 minutes.

The paste was placed in a relatively large amount of deionized water immediately following the formation thereof, and it was observed that the paste was non-dispersive in deionized water.

EXAMPLE 3

Organic Solvent Treatment 5 g of $CaHPO_4$ (DCPA) powder and 1.6 ml of 25 mM phosphoric acid aqueous solution were mixed, and stirred for one minute. To the resulting mixture 1.6 ml of acetone was added while stirring to form a paste followed by placing in a vacuum environment of −100 Pa for one hour, and the resulting dried mixture was mechanically ground for 20 minutes to fine particles. 1 g of the fine particles and 0.4 ml of phosphate aqueous solution (1.0 M, pH=6.0) were mixed to form a paste, which was tested every 30 seconds to determine the working time and the setting time. The working time of the paste of this example is 20.0 minutes and the setting time thereof is 22.0 minutes.

The paste was placed in a relatively large amount of deionized water immediately following the formation thereof, and it was observed that the paste was non-dispersive in deionized water.

EXAMPLE 4

Microwave Treatment 3 g of a mixed powder of $CaHPO_4$ (DCPA) and $Ca_4(PO_4)_2O$ (TTCP) in 1:1 molar ratio was mixed with 2.0 ml of 25 mM phosphoric acid aqueous solution, and the mixture was stirred for five minutes. The resulting mixture was placed in a microwave oven where it was heated under low power for five minutes. The resulting dried mixture was mechanically ground for 20 minutes to fine particles. 1 g of the fine particles and 0.42 ml of phosphate aqueous solution (1.0 M, pH=6.0) were mixed to form a paste, which was tested every 30 seconds to determine the working time and the setting time. The working time of the paste of this example is 2.0 minutes and the setting time thereof is 4.0 minutes.

The paste was placed in a relatively large amount of deionized water immediately following the formation thereof, and it was observed that the paste was non-dispersive in deionized water.

EXAMPLE 5

Heating Treatment 5 g of a mixed powder of DCPA and TTCP in 1:1 molar ratio was mixed with 1.6 ml of 25 mM phosphoric acid aqueous solution, and the mixture was stirred for one minute. The resulting mixture was placed in a high temperature oven at 500° C. for five minutes. The resulting dried mixture was mechanically ground for 20 minutes to fine particles. 1 g of the fine particles and 0.4 ml of phosphate aqueous solution (1.0 M, pH=6.0) were mixed to form a paste, which was tested every 30 seconds to determine the working time and the setting time. The working time of the paste of this example is 1.5 minutes and the setting time thereof is 2.5 minutes.

The paste was placed in a relatively large amount of deionized water immediately following the formation thereof, and it was observed that the paste was non-dispersive in deionized water.

EXAMPLE 6

Heating Treatment 5 g of a mixed powder of DCPA and TTCP in 1:1 molar ratio was mixed with 1.6 ml of 25 mM phosphoric acid aqueous solution, and the mixture was stirred for one minute. The resulting mixture was placed in a high temperature oven at 1000° C. for one minute. The resulting dried mixture was mechanically ground for 20 minutes to fine particles. 1 g of the fine particles and 0.4 ml of phosphate aqueous solution (1.0 M, pH=6.0) were mixed to form a paste, which was tested every 30 seconds to determine the working time and the setting time. The working time of the paste of this example is 31 minutes and the setting time thereof is 35 minutes.

EXAMPLES 7–11

The procedures of Example 1 were repeated except that the $Ca(H_2PO_4)_2.H_2O$ powder was replaced by a mixed powder of DCPA and TTCP in 1:1 molar ratio and the 25 mM phosphoric acid aqueous solution was replaced by a diluted phosphoric acid aqueous solution having a pH of 1.96. The heating treatments were carried out with conditions listed in Table 1. The performance is also listed in Table 1.

Control Example 1

1 g of a mixed powder of DCPA and TTCP in 1:1 mole and 0.4 ml of a diluted phosphoric acid aqueous solution having a pH of 1.96 were mixed to form a paste, which was tested every 30 seconds to determine the working time and the setting time. The paste of this example can not set within hours. The performance is listed in Table 1.

EXAMPLE 12

The procedures of Example 2 were repeated except that the DCPA powder was replaced by a mixed powder of DCPA and TTCP in 1:1 molar ratio and the 25 mM phosphoric acid aqueous solution was replaced by a diluted phosphoric acid aqueous solution having a pH of 1.96. The performance is listed in Table 1.

EXAMPLE 13

The procedures of Example 3 were repeated except that the DCPA powder was replaced by a mixed powder of DCPA and TTCP in 1:1 molar ratio and the 25 mM phosphoric acid aqueous solution was replaced by a diluted phosphoric acid aqueous solution having a pH of 1.96. The performance is listed in Table 1.

EXAMPLE 14

The procedures of Example 4 were repeated except that the 25 mM phosphoric acid aqueous solution was replaced by a diluted phosphoric acid aqueous solution having a pH of 1.96. The performance is listed in Table 1.

TABLE 1

| | Controlling treatment | Setting/working time (min) | Dispersive in water |
|---|---|---|---|
| Control Ex. 1 | — | — | Yes |
| Ex. 7 | Heating, 50° C. | 11.5/6.5 | No |
| Ex. 8 | Heating, 100° C. | 13.5/8.0 | No |
| Ex. 9 | Heating, 150° C. | 8.5/8.0 | No |
| Ex. 10 | Heating, 500° C. | 2.5/1.5 | No |
| Ex. 11 | Heating, 1000° C. | 35/31 | No |
| Lx. 12 | Vacuuming | 14.5/11.5 | No |
| Ex. 13 | Organic solvent | 17.5/16.5 | No |
| Ex. 14 | microwave | 3.5/2.5 | No |

Figure 6A:
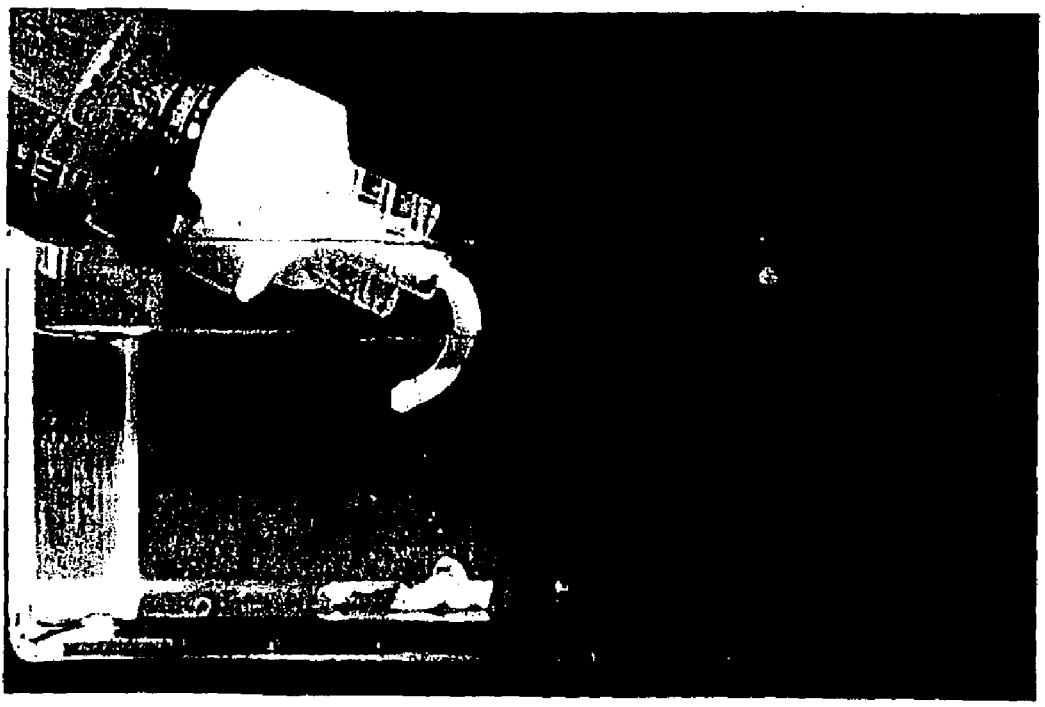
FIGS. 6a to 6c are photographs showing a CPC paste of the present invention injected into water via a syringe at 3, 10 and 30 seconds after the CPC paste being formed in accordance with the following Example 7.
Figure 6B:
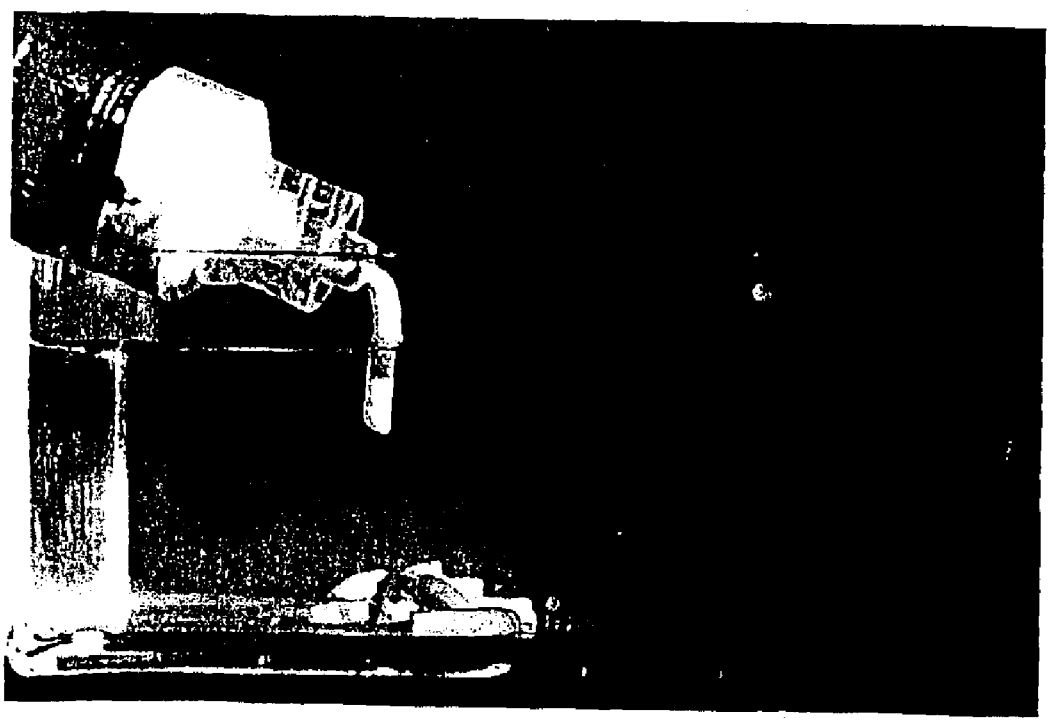
Figure 6C:
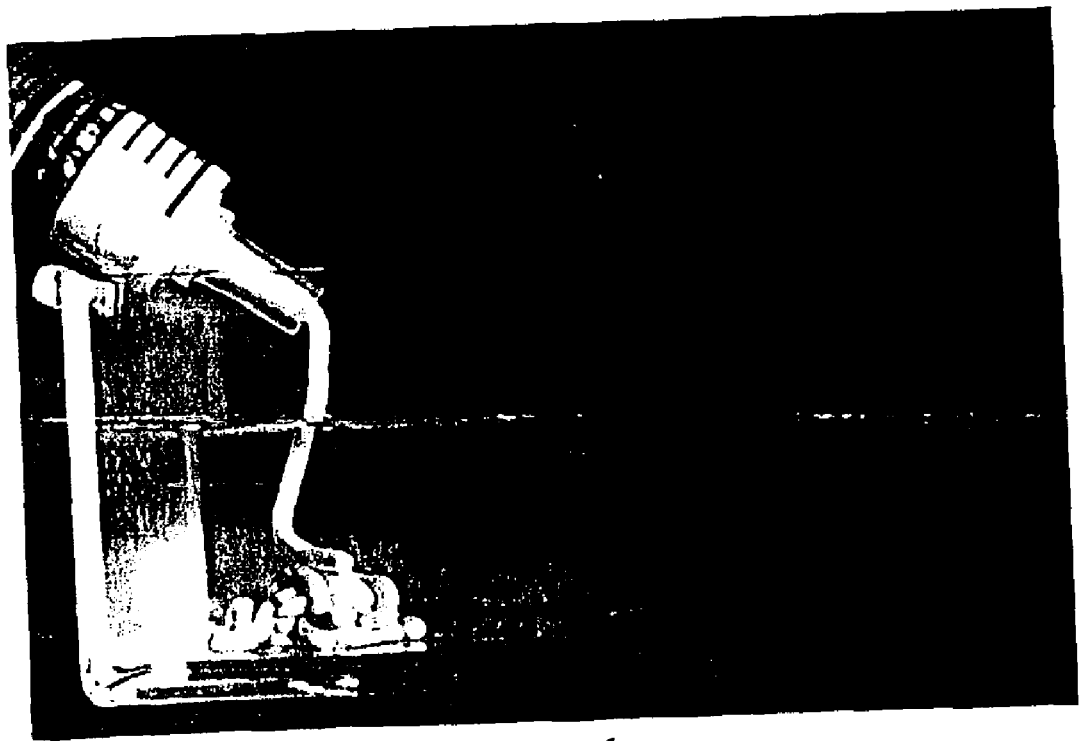

The pastes prepared in Control Example 1 and Example 7 were injected into water via a syringe at 3, 10 and 30 seconds after the paste being formed. The results are shown in FIGS. 5a to 5c and FIGS. 6a to 6c, respectively. It can be seen from FIGS. 5a to 5b that the paste prepared in Control Example 1 is dispersive in water. On the contrary, the paste prepared in Example 7 is non-dispersive as shown in FIGS. 6a to 6c.

Figure 7A:
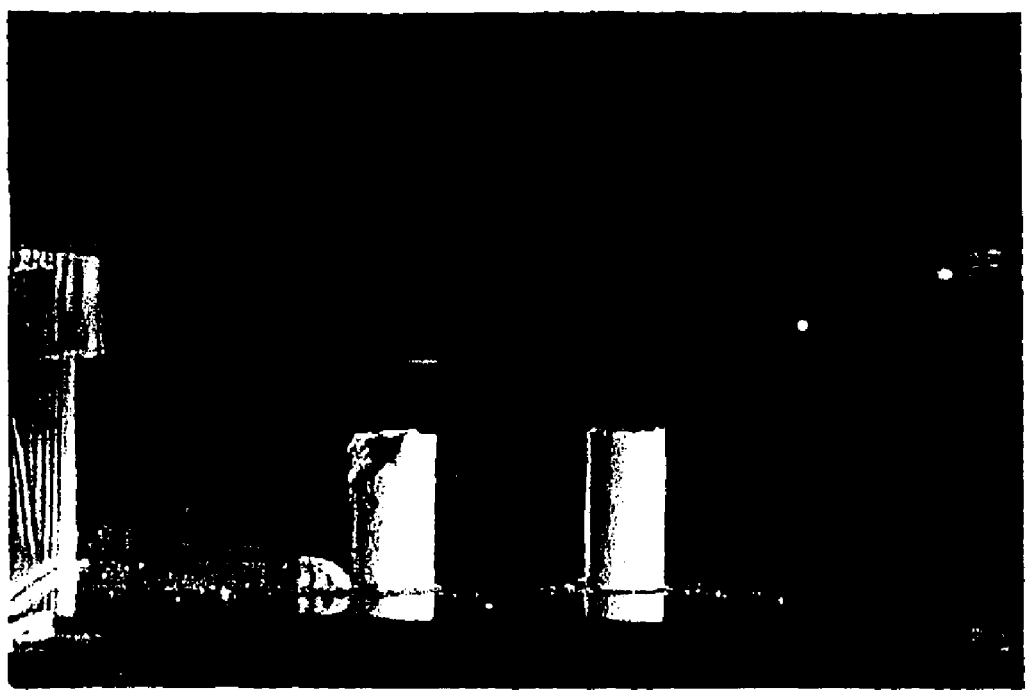
FIGS. 7a to 7c are photographs showing two cylinders prepared by separately molding a conventional CPC paste and a CPC paste of the present invention prepared in the following Example 7, which were taken at 5, 20 and 60 seconds after the two cylinders being immersed in the water.
Figure 7B:
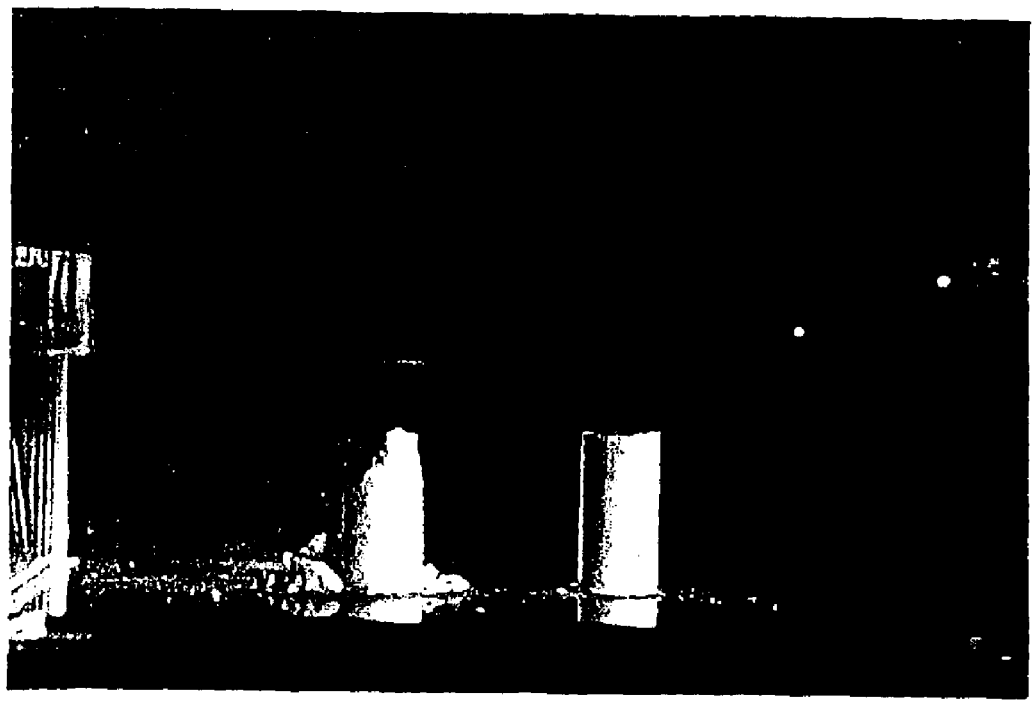
Figure 7C:
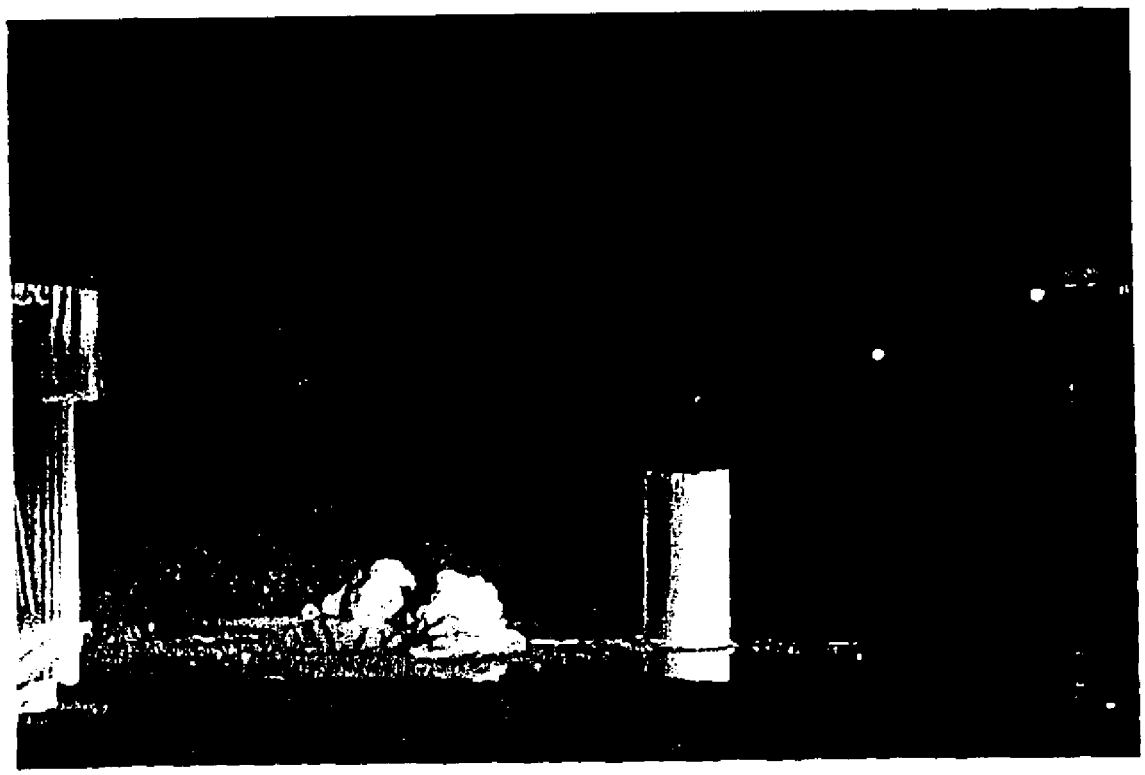
Figure 8:
FIG. 8 is a TEM micrograph showing the calcium phosphate cement of the present invention prepared in the following Example 7.
Figure 9:
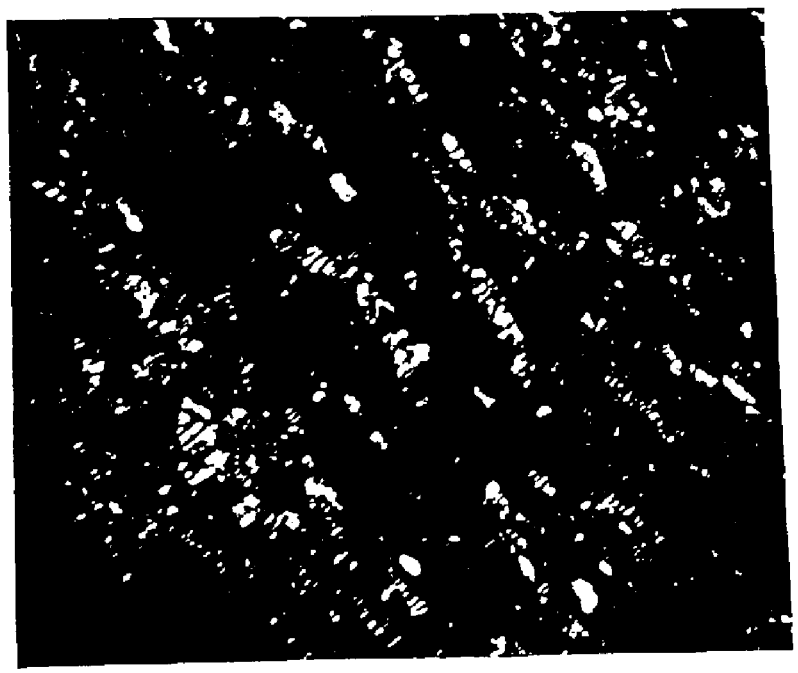
FIG. 9 is a TEM micrograph showing the calcium phosphate cement of the present invention prepared in the following Example 7.

Two cylinders were prepared by separately molding the pastes prepared in Control Example 1 and Example 7, and were then placed in water. FIGS. 7a to 7c show the pictures taken at 5, 20 and 60 seconds after the cylinders being immersed in the water, from which it can be seen that the left cylinder made from the paste prepared in Control Example 1 collapses, while the right cylinder made form the paste prepared in Example 7 remains almost intact.

It can be concluded from the results shown in FIGS. 5a to 7c that the paste prepared from the calcium phosphate cement of the present invention can be directly injected or implanted after being molded into a block into a cavity in a deformed tooth or bone.

Two samples of the calcium phosphate cement prepared in Example 7 were observed by transmission electron microscopy (TEM), and two TEM pictures (not shown in the drawings) indicate that there are whiskers on surfaces of calcium phosphate particles having different diameters of the calcium phosphate cement.

Figure 2:
FIG. 2 is a scanning electron microscopy (SEM) micrograph of the calcium phosphate cement prepared in accordance with Example 6 of the present invention.
Figure 3:
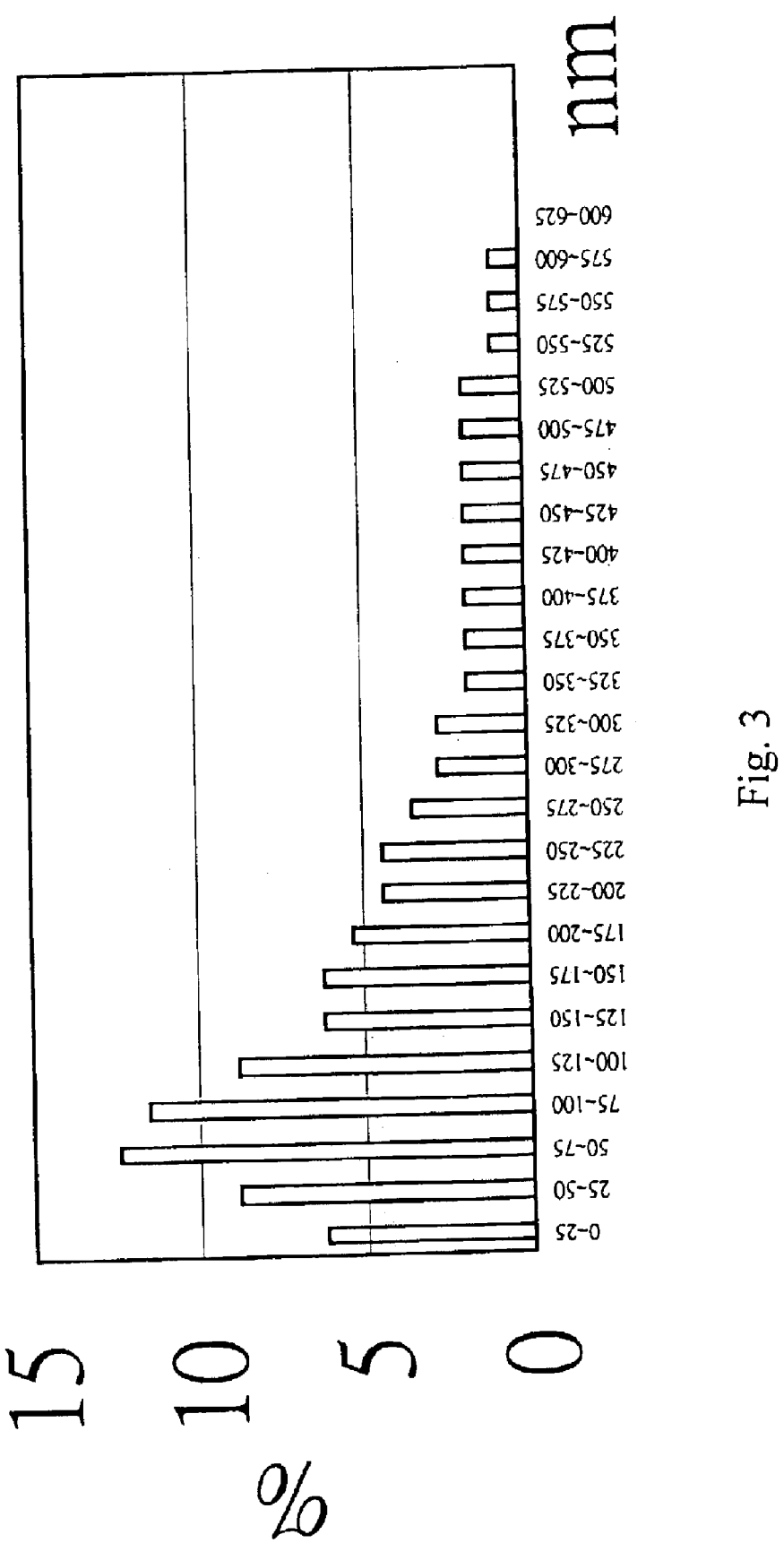
FIGS. 3 and 4 show the distributions of the lengths and the widths of the whiskers or fine crystals on surfaces of the calcium phosphate particles prepared in the following Example 6 of the present invention, respectively, which are determined directly from transmission electron microscopy (TEM).
Figure 4:
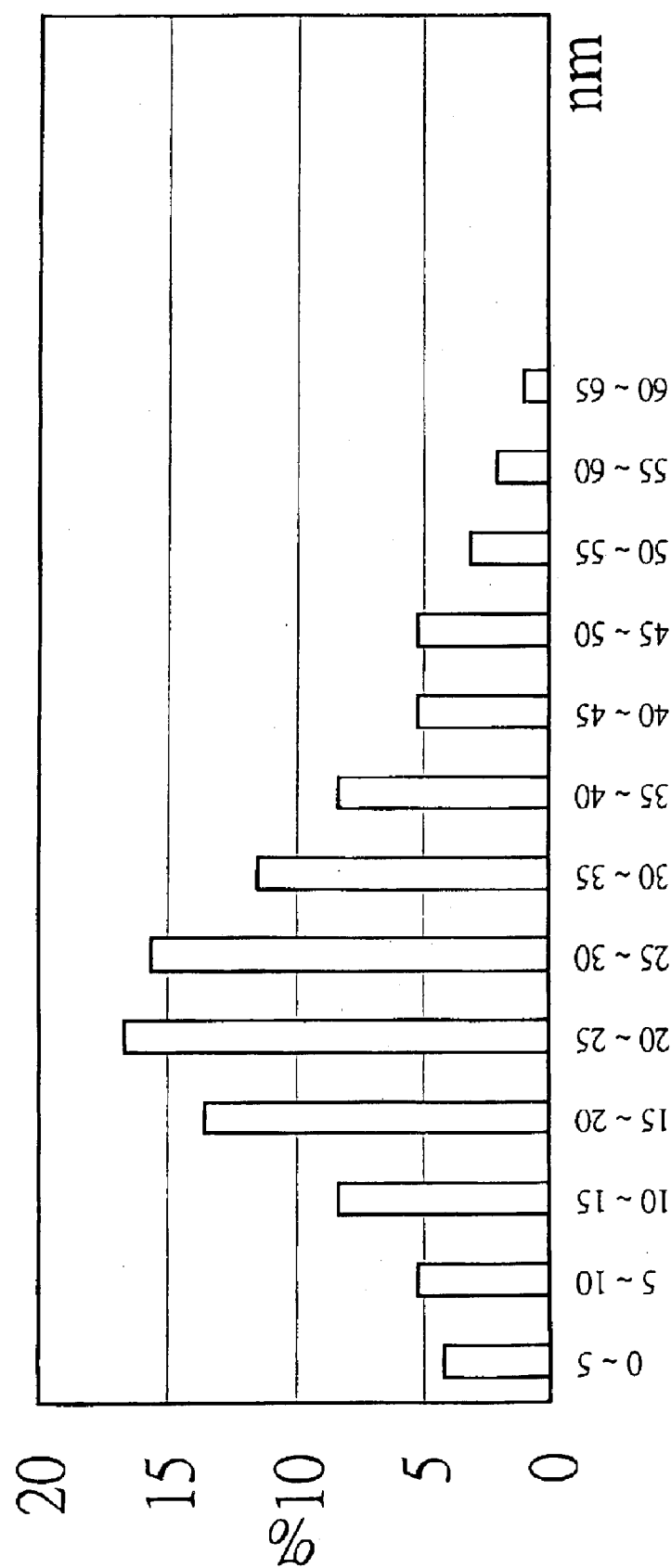
Figure 5A:
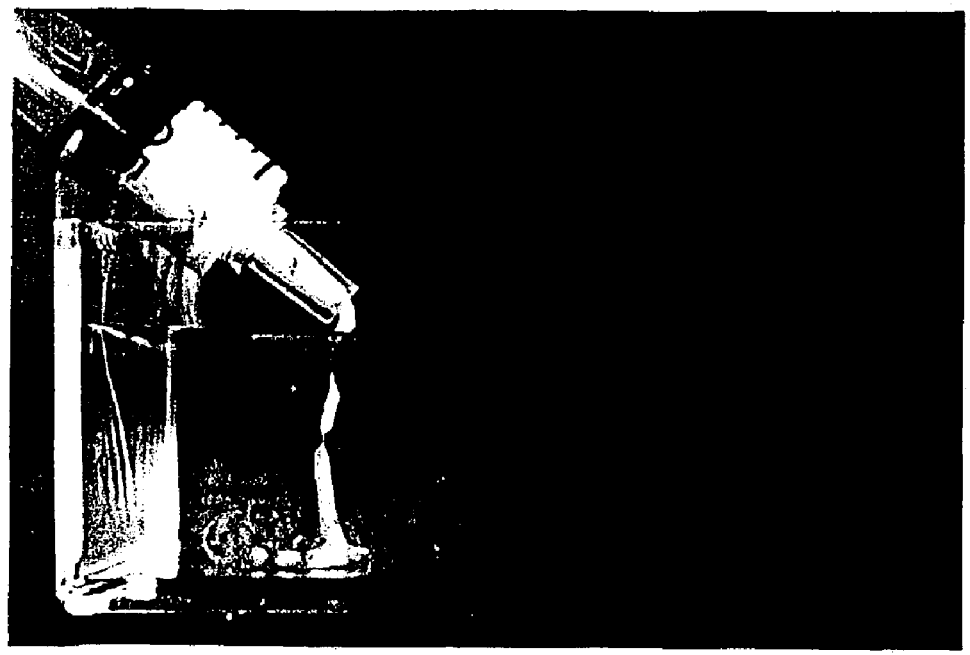
FIGS. 5a to 5c are photographs showing a conventional CPC paste injected into water via a syringe at 3, 10 and 30 seconds after the conventional CPC paste being formed.
Figure 5B:
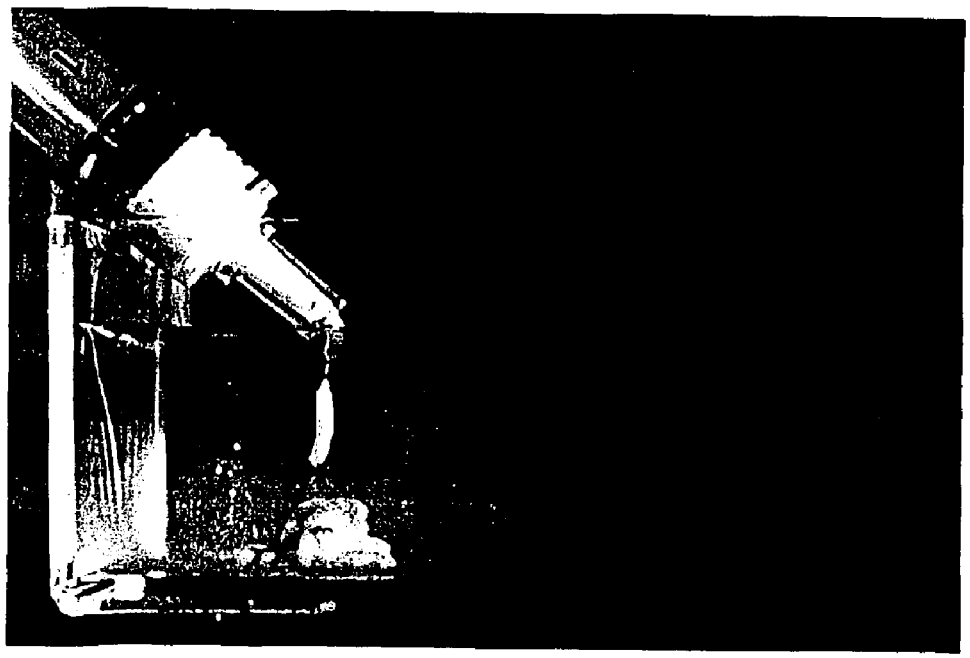
Figure 5C:

The calcium phosphate cement prepared in Example 6 has a particle diameter distribution shown in FIG. 1, which was determined by using particle size analyzer (Sald-2001, Shimadzu Co., Japan). The curve in FIG. 1 indicates that the particle diameters of the calcium phosphate cement prepared in Example 6 range from about 0.47 microns to 93.49 microns. FIG. 2 shows a scanning electron microscopy (SEM) micrograph of the calcium phosphate cement prepared in Example 6. Moreover, the lengths and the widths of the whiskers or fine crystals on surfaces of the calcium phosphate particles prepared in Example 6 were determined directly from TEM (JXA-840, JEOL Co., Japan), and the results are shown in FIGS. 3 and 4, respectively. As shown in FIGS. 3 and 4, the lengths and widths of the of the whiskers or fine crystals on surfaces of the calcium phosphate particles prepared in Example 6 range from 1 to 625 nm and 1 to 65 nm, respectively. Detailed microstructural/microchemical analysis indicates that the whiskers or fine crystals on surfaces of the calcium phosphate particles prepared in Example 6 are basic calcium phosphate. Energy dispersive spectroscopy (EDS) analysis was carried out on 15 such radically grown whiskers or fine crystals, and the Ca/P ratios thereof are from 1.35 to 2.18 with an average Ca/P ratio of 1.69 (standard deviation of 0.25).

EXAMPLES 15–19

The procedures of Example 7 were repeated by using the calcium phosphate powders and the wetting solutions listed in Table 2. The performance is also listed in Table 2.

TABLE 2

| | Calcium phosphate powder* | Wetting solution | Heating treatment | Setting/working time (min) | Dispersive in water |
|---|---|---|---|---|---|
| Ex. 15 | TCP | Phosphoric acid | Yes | 10/6.5 | No |
| Control Ex. 2 | TCP | — | No | — | Yes |
| Ex. 16 | TCP | Ethanol | Yes | 12.5/8.5 | No |
| Control Ex. 3 | TCP | — | No | — | Yes |
| Ex. 17 | TTCP + DCPA | Phosphoric acid | Yes | 11/8 | NO |
| Control Ex. 4 | TTCP + DCPA | — | No | — | Yes |
| Ex. 18 | TTCP + DCPA + TCP | Phosphoric acid | Yes | — | No |
| Control Ex. 5 | TTCP + DCPA + TCP | — | No | — | Yes |
| Ex. 19 | DCPA + TCP | Phosphoric acid | Yes | 29/24 | No |
| Control Ex. 6 | DCPA + TCP | — | No | — | Yes |

*TCP is anhydrous tricalcium phosphate.
TTCP + DCPA is a mixed powder of TTCP and DCPA in 1:1 molar ratio.
TTCP + DCPA + TCP is a mixed powder of TTCP + DCPA and TCP in 1:1 weight ratio.
DCPA + TCP is a mixed powder of DCPA and TCP in 1:2 molar ratio.

Control Examples 2–6

The procedures of Control Example 1 were repeated by using the calcium phosphate powders and the wetting solutions listed in Table 2. The performance is also listed in Table 2.

EXAMPLES 20–31

The procedures of Example 7 were repeated by using the wetting solutions having different pH values listed in Table 3. The performance is also listed in Table 3.

Control Examples 7–14

The procedures of Control Example 1 were repeated by using the wetting solutions having different pH values listed in Table 3. The performance is also listed in Table 3.

TABLE 3

|  | Wetting solution | pH | Heating treatment | Dispersive in water |
|---|---|---|---|---|
| Ex. 20 | Phosphoric acid | 0.56 | Yes | No |
| Control Ex. 7 | — | — | No | Yes |
| Ex. 21 | Phosphoric acid | 1.03 | Yes | No |
| Ex. 22 | Phosphoric acid | 1.17 | Yes | No |
| Ex. 23 | Phosphoric acid | 1.22 | Yes | No |
| Ex. 24 | Phosphoric acid | 1.32 | Yes | No |
| Ex. 25 | Phosphoric acid | 2.0 | Yes | No |
| Control Ex. 8 | — | — | No | Yes |
| Ex. 26 | Acetic acid + sodium carbonate | 7.0 | Yes | No |
| Control Ex. 9 | — | — | No | Yes |
| Ex. 27 | Sodium hydroxide | 9.5 | Yes | No |
| Control Ex. 10 | — | — | No | Yes |
| Ex. 28 | Sodium hydroxide | 12.55 | Yes | No |
| Control Ex. 11 | — | — | No | Yes |
| Ex. 29 | Acetic acid | 1.96 | Yes | No |
| Control Ex. 12 | — | — | No | Yes |
| Ex. 30 | Ethanol | — | Yes | No |
| Control Ex. 13 | — | — | No | Yes |
| Ex. 31 | Deionized water | 7.0 | Yes | No |
| Control Ex. 14 | — | — | No | Yes |

What is claimed is:

1. A calcium phosphate cement comprising calcium phosphate particles having a diameter of 0.05 to 100 microns, wherein said calcium phosphate particles on their surfaces have whiskers or fine crystals of basic calcium phosphate having a width ranging from 1 to 100 nm and a length ranging from 1 to 1000 nm.

2. The calcium phosphate cement according to claim 1, wherein said calcium phosphate particles have a diameter of 0.2 to 80 microns.

3. The calcium phosphate cement according to claim 1, wherein said whiskers or fine crystals have a width ranging from 2 to 70 nm and a length ranging from 5 to 800 nm.

4. The calcium phosphate cement according to claim 3, wherein said calcium phosphate particles have a diameter of 0.5 to 50 microns.

5. The calcium phosphate cement according to claim 4, wherein said whiskers or fine crystals have a length ranging from 10 to 700 nm.

6. The calcium phosphate cement according to claim 1, wherein said calcium phosphate particles have a molar ratio of calcium to phosphate ranging from 0.5 to 2.5.

7. The calcium phosphate cement according to claim 3, wherein said calcium phosphate particles have a molar ratio of calcium to phosphate ranging from 0.5 to 2.5.

8. The calcium phosphate cement according to claim 4, wherein said calcium phosphate particles have a molar ratio of calcium to phosphate ranging from 0.5 to 2.5.

9. The calcium phosphate cement according to claim 5, wherein said calcium phosphate particles have a molar ratio of calcium to phosphate ranging from 0.5 to 2.5.

10. The calcium phosphate cement according to claim 3, wherein said calcium phosphate particles have a molar ratio of calcium to phosphate ranging from 0.8 to 2.3.

11. The calcium phosphate cement according to claim 4, wherein said calcium phosphate particles have a molar ratio of calcium to phosphate ranging from 0.8 to 2.3.

12. The calcium phosphate cement according to claim 5, wherein said calcium phosphate particles have a molar ratio of calcium to phosphate ranging from 0.8 to 2.3.

13. The calcium phosphate cement according to claim 3, wherein said calcium phosphate particles have a molar ratio of calcium to phosphate ranging from 1.0 to 2.2.

14. The calcium phosphate cement according to claim 4, wherein said calcium phosphate particles have a molar ratio of calcium to phosphate ranging from 1.0 to 2.2.

15. The calcium phosphate cement according to claim 5, wherein said calcium phosphate particles have a molar ratio of calcium to phosphate ranging from 1.0 to 2.2.

16. A process for preparing a calcium phosphate cement comprising mixing a calcium phosphate powder or small pieces of calcium phosphate with a wetting agent, and controlling growth of whiskers or fine crystals of basic calcium phosphate on surfaces of said calcium phosphate powder or small pieces of calcium phosphate by a controlling treatment.

17. The process according to claim 16 further comprising grinding the resulting product from the controlling treatment to form calcium phosphate particles having a diameter of 0.05 to 100 microns, wherein said whiskers or fine crystals have a width ranging from 1 to 100 nm and a length ranging from 1 to 1000 nm.

18. The process according to claim 17, wherein said calcium phosphate particles have a diameter of 0.2 to 80 microns, and said whiskers or fine crystals have a width ranging from 2 to 70 nm and a length ranging from 5 to 800 nm.

19. The process according to claim 18, wherein said calcium phosphate particles have a diameter of 0.5 to 50 microns, and said whiskers or fine crystals have a length ranging from 10 to 700 nm.

20. The process according to claim 16, wherein said wetting agent is an aqueous solution containing more than 20 ppm of phosphoric acid or phosphate.

21. The process according to claim 20, wherein said wetting agent is an aqueous solution containing more than 50 ppm of phosphoric acid or phosphate.

22. The process according to claim 21, wherein said wetting agent is an aqueous solution containing more than 100 ppm of phosphoric acid or phosphate.

23. The process according to claim 16, wherein said controlling treatment is a vacuuming treatment, an organic solvent treatment, a microwave treatment or a heating treatment.

24. The process according to claim 20, wherein said controlling treatment is a vacuuming treatment, an organic solvent treatment, a microwave treatment or a heating treatment.

25. The process according to claim 21, wherein said controlling treatment is a vacuuming treatment, an organic solvent treatment, a microwave treatment or a heating treatment.

26. The process according to claim 22, wherein said controlling treatment is a vacuuming treatment, an organic solvent treatment, a microwave treatment or a heating treatment.

27. The process according to claim 26, wherein said calcium phosphate powder or said small pieces of calcium phosphate are soaked with said wetting agent, and said controlling treatment is a heating treatment comprising drying the resulting soaked calcium phosphate powder or soaked small pieces of calcium phosphate at a temperature higher than 45° C.

28. The process according to claim 26, wherein said calcium phosphate powder or said small pieces of calcium phosphate are soaked with said wetting agent, and said controlling treatment is a vacuuming treatment comprising drying the resulting soaked calcium phosphate powder or soaked small pieces of calcium phosphate under vacuum.

29. The process according to claim 26, wherein said calcium phosphate powder or said small pieces of calcium phosphate are soaked with said wetting agent, and said controlling treatment is a microwave treatment comprising drying the resulting soaked calcium phosphate powder or soaked small pieces of calcium phosphate by microwave heating.

30. The process according to claim 26, wherein said controlling treatment is an organic solvent treatment comprising mixing the mixture of said wetting agent and said calcium phosphate powder or small pieces of calcium phosphate with a water miscible organic solvent, and drying the resulting mixture under vacuum.

31. The process according to claim 17, wherein said calcium phosphate particles have a molar ratio of calcium to phosphate ranging from 0.5 to 2.5.

32. The calcium phosphate cement according to claim 1, wherein the whiskers or fine crystals of basic calcium phosphate have a molar ratio of calcium to phosphate ranging from 1.35 to 2.18.

33. The process according to claim 16, wherein the whiskers or fine crystals of basic calcium phosphate have a molar ratio of calcium to phosphate ranging from 1.35 to 2.18.

34. The process according to claim 17, wherein the whiskers or fine crystals of basic calcium phosphate have a molar ratio of calcium to phosphate ranging from 1.35 to 2.18.

* * * * *